US010324051B2

(12) United States Patent
Brosseau et al.

(10) Patent No.: US 10,324,051 B2
(45) Date of Patent: Jun. 18, 2019

(54) OPTICAL FLASH POINT DETECTION ON AN AUTOMATED OPEN CUP FLASH POINT DETECTOR

(71) Applicant: Petroleum Analyzer Company, LP, Houston, TX (US)

(72) Inventors: Michael Brosseau, Houston, TX (US); Thomas Herold, Boxberg-Uiffingen (DE); Simon Blass, Margetsoechheim (DE); Oezkan Oguz, Lauda-Koenigshofen (DE)

(73) Assignee: Petroleum Analyzer Company, LP, Houston, TX (US)

( * ) Notice: Subject to any disclaimer, the term of this patent is extended or adjusted under 35 U.S.C. 154(b) by 107 days.

(21) Appl. No.: 15/499,285

(22) Filed: Apr. 27, 2017

(65) Prior Publication Data
US 2018/0313774 A1 Nov. 1, 2018

(51) Int. Cl.
*G01N 25/50* (2006.01)
*G01N 21/33* (2006.01)
*G01N 25/52* (2006.01)

(52) U.S. Cl.
CPC .............. *G01N 25/50* (2013.01); *G01N 21/33* (2013.01); *G01N 25/52* (2013.01)

(58) Field of Classification Search
CPC ......... G01N 21/33; G01N 25/50; G01N 25/52
USPC .......................................................... 73/36
See application file for complete search history.

(56) References Cited

U.S. PATENT DOCUMENTS 3,011,337 A * 12/1961 McGlynn ............... G01N 25/52
                                                        219/201
5,869,343 A    2/1999 Handschuck et al.
5,932,796 A    8/1999 Arthaud et al.

OTHER PUBLICATIONS

Flame Sensor Uvtron R2868, "Quick Detection of FLme from Distance, Compact UV Sensor with High Sensitivity and Wide Directivity, Suitable for Flame Detectors and Fire Alarms," Hamamatsu. http://hamamatsu.com/jp/en/R2868.html.
"Open and Closed Cup Flash Point—What is the difference?", PEFTEC, Jun. 26, 2014, https://www.petro-online.com/news/analytical-instrumentation/11/breaking_nws/open_a . . . .
"Standard Test Method for Flash and Fire Points by Cleveland Open Cup Tester", Designation: D92-16, ASTM International, Dec. 13, 2016.
"Vapor," Wikipedia, https://en.wikipedia.org/wiki/Vapor.
"Fire Point," https://en.wikipedia.orga/wiki/Fire_point.
"Clevelan open-cup method," https://en.wikipedia.org/wiki/Cleveland_open-cup_method.

* cited by examiner

*Primary Examiner* — Benjamin R Schmitt
(74) *Attorney, Agent, or Firm* — Snyder, Clark, Lesch & Chung, LLP

(57) ABSTRACT

An open cup flash point detector is shown that rapidly increases the temperature of the substance being tested until temperature is close to a theoretical flash point. Thereafter, as temperature is slowly increased, an igniter flame moves in an arc over the upper lip of the test cup while simultaneously a UV sensor senses a wedge-shaped area, also immediately over the upper lip of the test cup. The arc of the igniter flame and the wedge-shaped area do not overlap. By incremental increases in temperature and repeating the arc movement of the igniter flame, the flash point can be detected by the UV sensor.

6 Claims, 3 Drawing Sheets

OPTICAL FLASH POINT DETECTION ON AN AUTOMATED OPEN CUP FLASH POINT DETECTOR

BACKGROUND OF THE INVENTION

1. Field of the Invention

The present invention relates to flash point detection and, more particularly, to a method and apparatus for optical flash point detection in an open cup tester.

2. Description of the Prior Art

The term "flash point" is the lowest temperature at which a volatile substance can be vaporized into a flammable gas. To measure the flash point, an ignition source has to be introduced to the substance with the "flash" being the point at which the vapor is ignited. While there are various methods of measuring the flash point, those methods can generally be divided into two main categories: open and closed cup flash points.

Measuring a flash point using an open cup method is conducted in a vessel which is exposed to the air outside. Temperature of a substance being tested is rapidly raised until the temperature approaches the theoretical flash point, after which the temperature is gradually raised with an ignition source being periodically passed over the top of the substance. When the substance reaches a temperature at which it "flashes" and ignites, the true "flash point" has been reached. The most commonly-used open cup method is called the Cleveland open cup. There is a published standard by the American Society of Testing and Materials (ASTM) entitled "Standard Test Method for Flash and Fire Points by Cleveland Open Cup Tester," ASTM D92-16A. The flash point of a substance may vary according to the distance between the substance being measured and the ignition source, i.e., the height of the flame above the cup.

The closed cup flash point detector, as the name suggests, uses a closed cup with the substance being tested being inside a closed container which is not open to outside atmosphere. A lid is sealed in place over the substance being tested and the ignition source is introduced into the vessel itself. There are four general kinds of closed cup flash point detectors, Pensky Martens, Abel, Tag and Small Scale (also known as Setaflash).

As automated test equipment started being developed, the industry adopted an ionization ring as a method of detecting the flash point. The ionization ring would sit inside the test cup between the sample and the ignition source. The ionization ring would sense a charge caused by the ignition. There were drawbacks to using the ionization ring method of detection of flashpoint. Some samples being measured expand as they are heated, which expansion may cause contact with the ionization ring and give a false signal. Samples with high water content also give a false flash point signal. Other samples such as silicon oils produce vapors that coat the ionization ring, which insulates the ionization ring so that it does not sense the ignition. Failing to sense the ignition creates a safety issue because the detector will continue to heat the sample.

In using the Cleveland open cup method, a test cup (usually brass) is filled to a certain level with the substance being measured. Then, the temperature of the substance being measured is increased rapidly until it approaches the theoretical flash point. Thereafter, the temperature is increased at a slow constant rate as it approaches the theoretical flash point. The increase in temperature of the substance being tested will cause the substance to produce flammable vapor in increasing quantities and density. The lowest temperature at which a small test flame passed over the surface of a liquid causes the vapor from the liquid to ignite is considered the substance flash point.

The "fire point" of a substance is the lowest temperature at which the vapor of that substance will continue to burn for at least five (5) seconds after ignition by an open flame. At the "flash point," a lower temperature, a substance will ignite briefly, but vapor is not being produced at a rate to sustain the fire. Most tables of material properties only list the flash points. Generally, the fire points of a substance are about ten degrees Centigrade (10° C.) higher than the flash points.

A related patent over which this invention is an improvement is U.S. Pat. No. 5,932,796 issued on Aug. 3, 1999, entitled "Apparatus for the Determination of a Flash Point of a Substance" by Arthaud et al., which related patent is incorporated by reference. However, the '796 patent has some problems that affect its accuracy. The flame 5 is located some distance above the substance 2 being tested, which affects the measurement. Further, the flame 5 may cause false readings indicating that a flash point has been reached.

SUMMARY OF THE INVENTION

It is an object of the present invention to provide for optical flash point detection using an open cup method.

It is another object of the present invention to provide for optical flash point detection using an ultraviolet (UV) detector.

It is yet another object of the present invention to provide an optical flash point detector that minimizes interference from other light sources.

It is even another object of the present invention to use an UV detector located in special housing that allows the UV detector to scan the surface of a wedge-shaped portion of a cup containing the substance being tested for flash point.

It is still another object of the present invention to provide a method and apparatus for detecting flash point of a substance being tested without interference from the igniter flame.

It is another object of the present invention to provide an apparatus and method where the igniter flame can skim a portion of the surface of the substance being tested while simultaneously an ultraviolet detector scans a different portion of the surface of the substance being tested without ever receiving interfering light from the igniter flame.

A stand is provided that has a test cup mounted in the upper surface of the stand with a heating element being located there below. At predetermined intervals, an igniter flame swings back and forth over the top of the test cup in a predefined arc. A UV sensor is provided inside of a UV sensor mount that allows the UV sensor to have a viewing angle immediately above the test cup that is adjacent to, but does not overlap, the arc of the igniter flame.

The temperature of the substance being tested inside of a test cup is raised very rapidly until it approaches the theoretical flash point after which the substance is heated in a manner to cause a slower rise in temperature. During the slower rise in temperature, periodically an igniter flame will swing across the surface of the test cup. This is done automatically with a computer supplying the gas to the igniter, lighting the igniter and causing the igniter to swing from side-to-side. Also, the computer measures the temperature and the output of the UV sensor, all of which is stored on a recording display or other suitable electronic storage device.

The UV sensor mount is especially designed so that the UV sensor can only see a predefined wedge-shaped area just above the test cup, which is adjacent to, but does not include, the igniter flame.

The UV sensor mount has an optical system of lens and slits receiving a converging beam of light, also called a collimator.

DESCRIPTION OF THE PREFERRED EMBODIMENT

Figure 1:
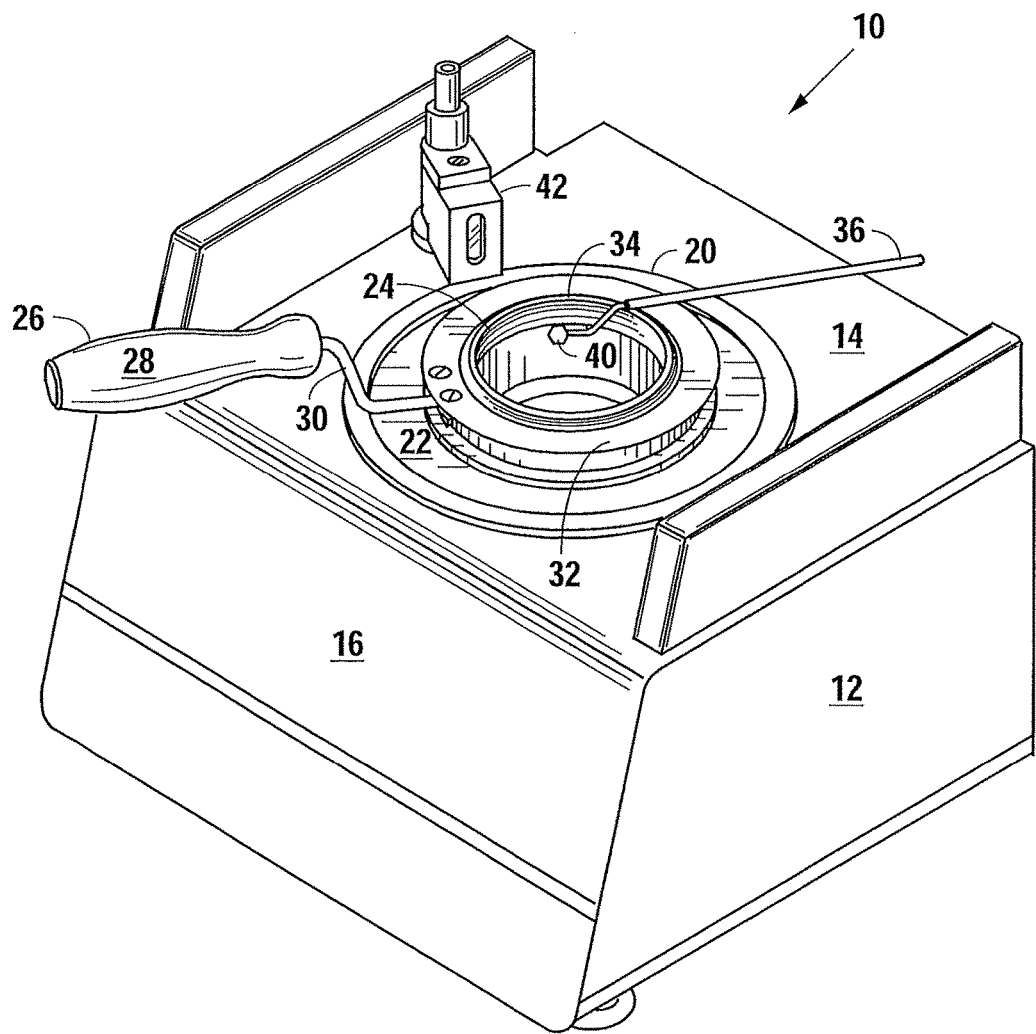
FIG. 1 is a perspective view of the mechanical portion of an open cup flash point detector.
Figure 2:
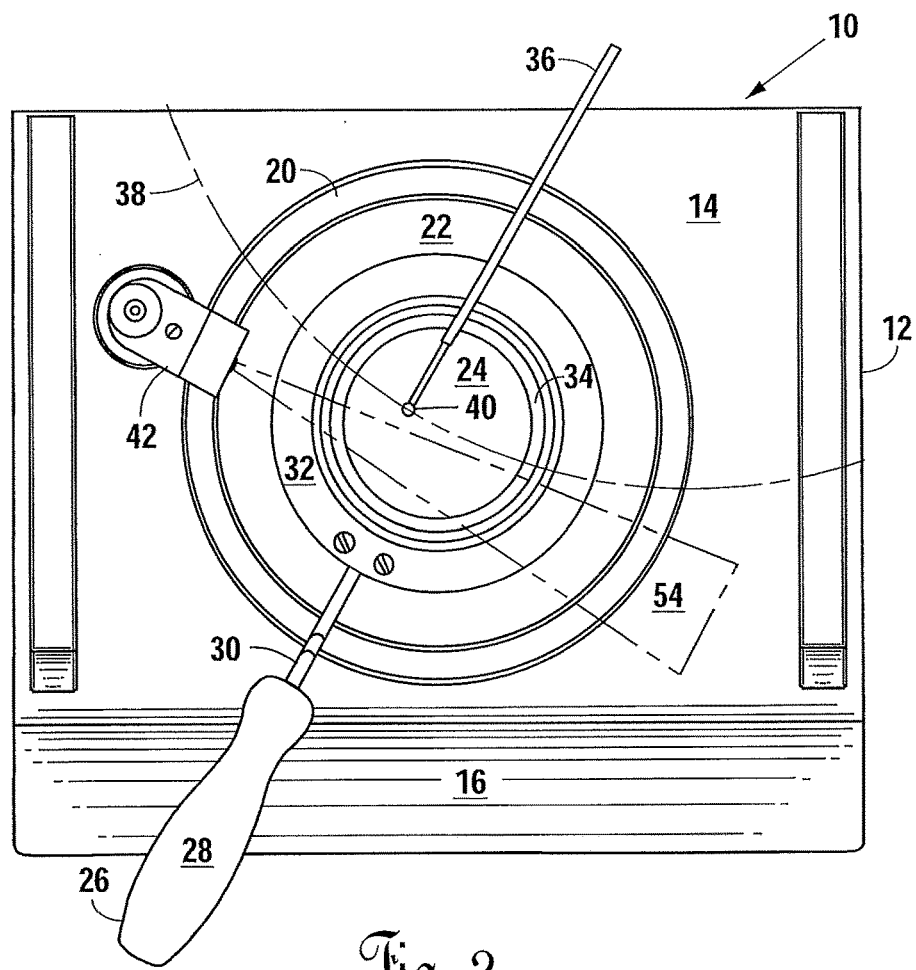
FIG. 2 is a top view of FIG. 1, illustrating movement of the ignitor flame and viewing area of a UV sensor from a collumator.

Referring to FIGS. 1 and 2 in combination, an open cup flash point detector 10 is shown. More detail on open cup flash point detectors can be found in ASTM D92-16A, entitled "Standard Test Method for Flash and Fire Points by Cleveland Open Cup Tester."

The open cup flash point detector 10 has a stand 12 with an upper surface 14. Vertical walls 16 enclose the stand 12 and support the upper surface 14.

Thermal insulation arranged in a cylinder shape with an upper rim 20 is inserted in a circular opening (not shown) in the upper surface 14 of the open cup flash point detector 10. The upper rim 20 holds the thermal insulation extending there below, which upper rim 20 is supported by the upper surface 14.

A retaining ring 22 is located inside of the upper rim 20, which retaining ring 22 has a center opening just large enough to receive therein a test cup 24, which test cup 24 meets the requirement of ASTM D92-16A.

Below the test cup 24 inside of the enclosure 16 is a heater (not shown) that is used to heat the test cup 24. Because the test cup 24 gets hot, a test cup holder 26 is provided. The test cup holder 26 has an insulated handle 28, connecting rod 30 and pick-up ring 32. The pick-up ring 32 is part of the test cup 24.

Located just above the upper lip 34 of the test cup 24 is an igniter arm 36. The igniter arm 36 periodically swings back and forth in the arc 38 illustrated in FIG. 2. On the tip 40 of the igniter arm 36 will be an igniter flame. The reach of the igniter flame is defined by the arc 38, which igniter flame is just above the upper lip 34 of the test cup 24.

Also located on the upper surface 14 of the open cup flash point detector 10 is a collumator 42. The internal design of the collumator 42 is shown in the vertical cross-sectional view of FIG. 3. The collumator 42 includes an ultraviolet (UV) sensor 44 located inside of chamber 46. Connecting to the chamber 46 and the UV sensor 44 is a slot 48 in the collumator 42. At one end of the slot 48 is located the UV sensor 44. At the other end of the slot 48 are located lens 50, which lens 50 have a beam opening 52 therein. The beam opening 52 will allow light outside the collumator 42 that travels through beam opening 52 to reach the UV detector 44. A wedge-shaped area 54 defines the area sensed by the UV sensor 44 in collumator 42. The arc 38 of the igniter flame never touches the wedge-shaped area 54. This prevents any false triggering of the UV sensor 44 by the igniter flame from tip 40.

While many different types of UV sensors 44 may be used, the Hamamatsu R286A flame sensor sold under the mark UVTRON has been found to work satisfactorily in the present invention. R2868 is a UVTRON ultraviolet ON/OFF detector that makes use of photo electric effect. It has a narrow spectrum sensitivity of between 185 nm to 260 nm and is insensitive to visible light.

While not shown in FIGS. 1 and 2, a thermometer would be inserted inside of the test cup 24. The substance to be measured would fill the test cup 24 so that the tip 40 of the igniter arm 36 swings back and forth just above a surface of the liquid being tested.

Figure 3:
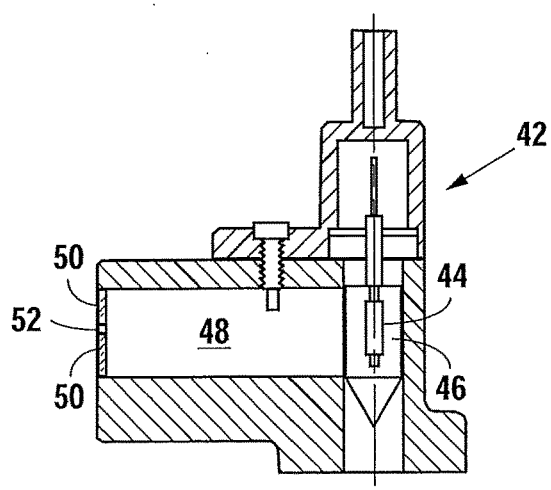
FIG. 3 is a vertical cross-sectional view of the collumator shown in FIGS. 1 and 2.
Figure 4:
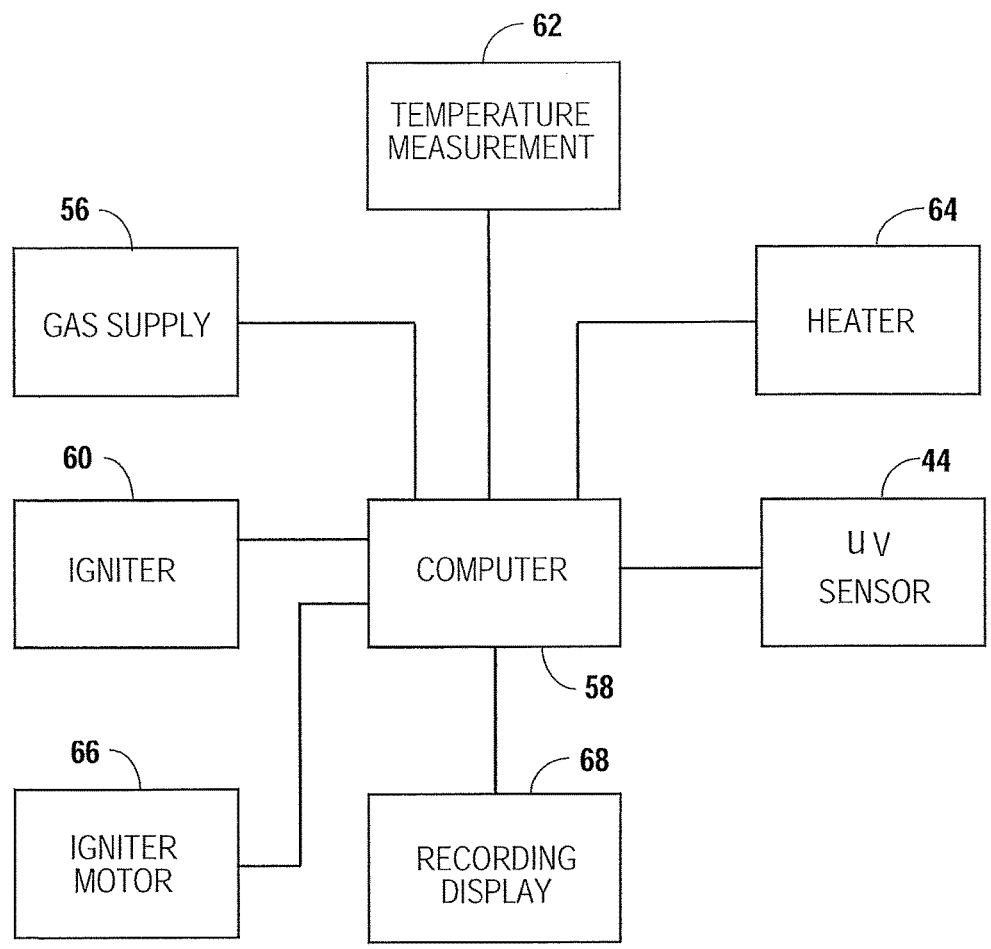
FIG. 4 is an illustrative block diagram of controls for the open cup flash point detector shown in FIGS. 1 and 2.

The open cup flash point detector 10, as shown in FIGS. 1-3, can be automated as shown in FIG. 4 by having a gas supply 56 turned on by computer 58 and ignited by igniter 60. The fluid being measured in the test cup 24 is continually monitored by a temperature measurement 62.

Initially, the computer 58 will turn on a heater 64 that will heat the liquid contained in the test cup 24. The heater 64 may be a resistance type heater or may use gas from the gas supply 56. Initially, the substance being tested in the test cup is raised in temperature very rapidly by the heater 64. As the substance being tested in the test cup 24 nears the theoretical flash point, the amount of heat being applied by the heater 64 is reduced. Thereafter, as the substance being tested is increased in temperature a slight amount (such as one or two degrees), by further application of heat from the heater 64. An igniter motor 66 is turned ON to swing the igniter 60 over the test cup 24, which igniter 60 has a flame on the tip 40 thereof.

If the substance being tested does not ignite as is determined by UV sensor 44, computer 58 causes the heater 64 to continue to slowly increase the temperature of the substance in the test cup 24 as is determined by temperature measurement 62. After the temperature of the substance being tested is raised another increment, the process is repeated where the igniter motor 66 again swings the tip 40 of the igniter arm 36 over the upper surface of the test cup 24.

Again, if the UV sensor 44 does not detect a flash of the substance being tested, the process will again be repeated. These steps are repeated in incremental increases of temperature until the substance being tested flashes as detected by the UV sensor 44. All of the steps undertaken in the open cup flash point detector 10 are recorded in a recording display 68 or a similar electronic storage device.

The UV sensor 44 receives light from a wedge-shaped area 54 that extends just over the upper lip 34 of the test cup 24. The wedge-shaped area 54 is immediately adjacent to the arc 38 of the igniter flame, but the two do not overlap. In this manner, the igniter flame moving in an arc 38 can never cause a false triggering of the UV detector 44. The shape of the wedge-shaped area 54 is determined by the lens 50 and the beam opening 52 as contained in the collumator 42.

What we claim is:

1. A flash point detector for determining a flash point of a substance being tested using an open cup method, said flash point detector having a source of power and a source of gas, said flash point detector including:
   a stand having an upper surface with an opening in said upper surface;
   a test cup located in said opening;

a heater connected to said source of power and located below said test cup for heating said test cup and said substance contained therein;

insulation for thermally insulating said test cup and said heater from said stand;

a test cup holder adjacent said test cup for picking up said test cup when hot;

an igniter connected to said gas source for generating an ignitor flame immediately above said test cup; and an ultraviolet (UV) detector in a collumator located on said upper surface beside said opening;

said ignitor flame periodically swinging in an arc immediately above said test cup;

said collumator restricting a monitoring area of said UV detector to a wedge-shaped area immediately above said test cup;

said arc being adjacent to, but not overlapping, said wedge-shaped area; and said UV detector detecting when said substance reaches the flash point.

2. The flash point detector as recited in claim 1 wherein said collumator has a chamber where said UV detector is located, and a slot from said chamber to a lens with a beam opening therein, said beam opening allowing the receiving of light from said wedge-shaped area.

3. The flash point detector as recited in claim 2 wherein between said periodically swinging of said ignitor flame, a temperature of said substance is incrementally increased.

4. The flash point detector as recited in claim 3, wherein the flash point detector is configured to:

recording record each temperature where said igniter flame swings immediately above said test cup and record at what temperature said UV detector detects said flash point.

5. A method of operation of an open cup flash point detector to determine a flash point of a substance, said method of operation including:

placing a test cup of said substance in an upper opening of a test stand;

continuously measuring a temperature of said substance in said test cup;

rapidly increasing the temperature of said substance in said test cup until said substance approaches a theoretical flash point;

thereafter, slowly increasing temperature of said substance in said test cup;

periodically swinging an igniter flame in an arc just above said test cup;

monitoring a wedge-shaped area just above said test cup with a UV detector to detect when said substance flashes; and recording the temperature of said substance when said substance flashes;

said arc and said wedge-shaped area are adjacent and above said test cup, but not overlapping.

6. The method of operation of an open cup flash point detector as recited in claim 5 wherein said monitoring step includes locating said UV detector in a chamber of a collumator connected by a slot to a lens with a beam opening to allow ultraviolet light from said wedge-shaped area to enter said collumator, said wedge-shaped area being just above said test cup.

* * * * *

UNITED STATES PATENT AND TRADEMARK OFFICE
CERTIFICATE OF CORRECTION

PATENT NO. : 10,324,051 B2
APPLICATION NO. : 15/499285
DATED : June 18, 2019
INVENTOR(S) : Michael Brosseau et al.

It is certified that error appears in the above-identified patent and that said Letters Patent is hereby corrected as shown below:

In the Claims

Column 6, Line 1 in Claim 4, delete "recording"

Signed and Sealed this
Thirteenth Day of August, 2019

Andrei Iancu
*Director of the United States Patent and Trademark Office*